(12) United States Patent
Matsuura et al.

(10) Patent No.: US 8,740,979 B2
(45) Date of Patent: Jun. 3, 2014

(54) SYSTEM AND METHOD FOR RESTORATION OF NUTRIENT FLOW TO NUCLEUS PULPOSA

(75) Inventors: David G. Matsuura, Encinitas, CA (US); Walter Dean Gillespie, San Diego, CA (US); Philip J. Simpson, Escondido, CA (US)

(73) Assignee: Flex Partners, Inc., Solana Beach, CA (US)

( * ) Notice: Subject to any disclaimer, the term of this patent is extended or adjusted under 35 U.S.C. 154(b) by 1059 days.

(21) Appl. No.: 11/916,641

(22) PCT Filed: Jun. 7, 2006

(86) PCT No.: PCT/US2006/022053
§ 371 (c)(1),
(2), (4) Date: Dec. 5, 2007

(87) PCT Pub. No.: WO2006/133256
PCT Pub. Date: Dec. 14, 2006

(65) Prior Publication Data
US 2008/0215152 A1    Sep. 4, 2008

Related U.S. Application Data

(60) Provisional application No. 60/688,299, filed on Jun. 7, 2005.

(51) Int. Cl.
*A61F 2/44* (2006.01)
(52) U.S. Cl.
USPC ........................................ 623/17.12; 604/522

(58) Field of Classification Search
USPC ................. 623/17.11–17.16; 604/500, 522
See application file for complete search history.

(56) References Cited

U.S. PATENT DOCUMENTS

| | | | |
|---|---|---|---|
| 6,056,749 A * | 5/2000 | Kuslich | 606/86 A |
| 6,086,589 A * | 7/2000 | Kuslich et al. | 606/247 |
| 6,533,817 B1 | 3/2003 | Norton et al. | |
| 6,607,530 B1 * | 8/2003 | Carl et al. | 606/914 |
| 2001/0023349 A1 * | 9/2001 | VanTassel et al. | 606/53 |
| 2003/0158557 A1 * | 8/2003 | Cragg et al. | 606/86 |
| 2004/0210209 A1 * | 10/2004 | Yeung et al. | 604/500 |
| 2004/0215343 A1 | 10/2004 | Hochschuler et al. | |
| 2004/0230195 A1 * | 11/2004 | Kaikkonen et al. | 606/72 |
| 2005/0246023 A1 * | 11/2005 | Yeung | 623/17.11 |
| 2006/0122704 A1 * | 6/2006 | Vresilovic et al. | 623/17.16 |
| 2006/0206209 A1 * | 9/2006 | Cragg et al. | 623/17.16 |
| 2006/0247600 A1 * | 11/2006 | Yeung et al. | 604/500 |
| 2007/0067025 A1 * | 3/2007 | Schwartz | 623/1.39 |

* cited by examiner

*Primary Examiner* — Pedro Philogene
*Assistant Examiner* — Lynnsy Schneider
(74) *Attorney, Agent, or Firm* — Knobbe, Martens, Olson & Bear LLP

(57) ABSTRACT

Disclosed are methods and devices for restoring or establishing nutrient flow to the nucleus pulposa. An implant comprises a nutrient flow path for extending between a source of nutrients and the nucleus pulposa. The implant is positioned within the patient such that a first end is in nutrient flow communication with a subject nucleus pulposa, and the source end is positioned in nutrient flow communication with a source of nutrients.

12 Claims, 9 Drawing Sheets

SYSTEM AND METHOD FOR RESTORATION OF NUTRIENT FLOW TO NUCLEUS PULPOSA

CROSS-REFERENCE TO RELATED APPLICATIONS

This application is a U.S. National Phase of International Application No. PCT/US2006/022053, filed Jan. 7, 2006, designating the U.S. and published in English on Dec. 14, 2006 as WO 2006/133256, which claims the benefit of U.S. Provisional Application No. 60/688,299, filed Jun. 7, 2005.

BACKGROUND OF THE INVENTION

Field of the Invention

The present invention relates to methods and apparatus for restoration of nutrition to the nucleus pulposa or other avascular body tissues such as joint cartilage, by placement of a device or material that promotes nutrient flow into disc tissue from the vertebral body, other skeletal structures, or surrounding tissue.

SUMMARY OF THE INVENTION

As a result of the certain disease states, the subchondral bone cartilaginous endplate becomes impermeable to nutrient transfer to, and removal of waste metabolites from the nucleus pulposa. The increasingly oxygen and glucose starved cellular matrix of the nucleus pulposa decreases in pH until its normal physiological processes are interrupted. As a result, the osmotic gradient into the disc is reduced which leads to decreasing water content in the nucleus pulposa. A dehydrated nucleus pulposa places more stress upon the surrounding annular tissue, leading to fissures and herniation. Eventually, the degenerated disc may cause significant discomfort or disability so that major surgical intervention such as total disc replacement or spinal fusion is required.

Methods and devices are disclosed that provide a technique for restoration of nutrient transfer from the vertebral body and surrounding tissues, via the vertebral body endplate, to the nucleus pulposa. Successful restoration of nutrient transfer to the nucleus pulposa would interrupt the progression of disc degeneration and restore normal function to the disc. All three methods summarized here for treatment of the diseased disc would employ minimally invasive surgical techniques for creating an access portal in the vertebral body adjacent to the diseased disc. No disruption of the annulus would be required for these procedures. For the first method, a portion of the endplate would then be removed and a device which facilitates transport of nutrients from the vertebral body cancellous bone would be inserted in the cavity. The distal end of the device would be placed in contact with the nucleus pulposa. Any portion of the cavity that the device does not occupy will be back filled to prevent undesired motion of the device. For the second method, all or nearly all of the subchondral bone-cartilaginous endplate would be removed and replaced with a device which facilitates transport of nutrients from the vertebral body cancellous bone to the nucleus pulposa such as a sintered porous stainless steel puck or osmotic membrane. Cancellous bone material removed to gain access to the endplate would be backfilled to prevent un-desired motion of the device For the third method the endplate would be ported with a multiplicity of small holes. The cavity in the vertebral body created to access the endplate would be filled with a material that would facilitate transport of nutrients from the vertebral body and surrounding tissues.

Thus, the present invention provides methods and devices for establishing a nutrient flow channel between a first side and a second side of a boney barrier. In the disclosed implementations of the invention, the boney barrier is a vertebral body end plate. In accordance with the method of the present invention, a passageway is formed through the bone barrier, to permit the transport of nutrients therethrough. A device may be installed within the passageway, such that a first end of the device is in communication with a target tissue such as nucleus pulposa, and a second end of the device is in communication with a nutrient source. The nutrient source may be the cancellous bone of an adjacent vertebral body, a natural source of nutrients outside of the vertebral body, or an implanted source of nutrients. The device includes at least one flow path between the first and second ends, to facilitate the transport of nutrient therethrough.

DETAILED DESCRIPTION OF THE PREFERRED EMBODIMENT

Figure 1A:
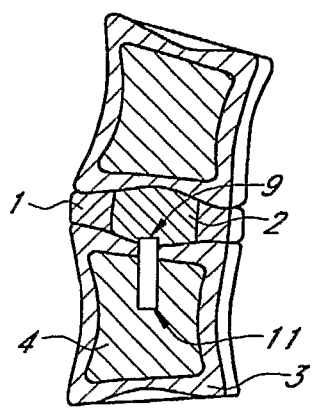
FIG. 1 illustrates the three proposed pathways for restoring nutrient flow to the annulus pulposa.
Figure 1B:
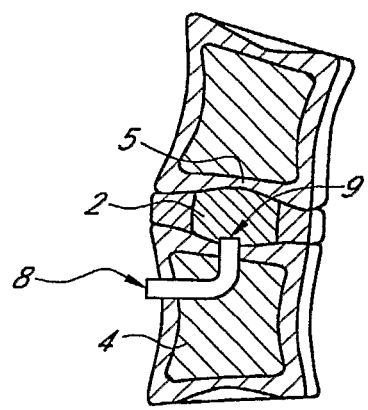
Figure 1C:
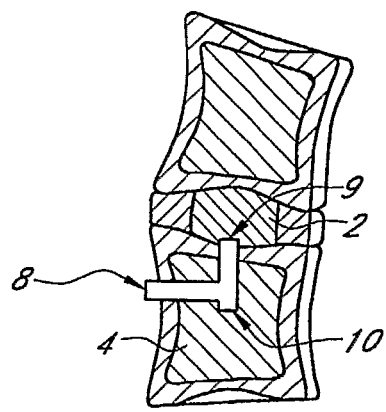

Referring to FIG. 1, three potential pathways for nutrient transfer to the nucleus pulposa 2 are illustrated: A first route from the cancellous bone material 4 which occupies the center of the vertebral body, to the nucleus pulposa 2, a second route from the tissues surrounding the vertebral body 8, via the vertebral body endplate 5 to the nucleus pulposa 2, and a third route from both regions simultaneously.

Figure 2:
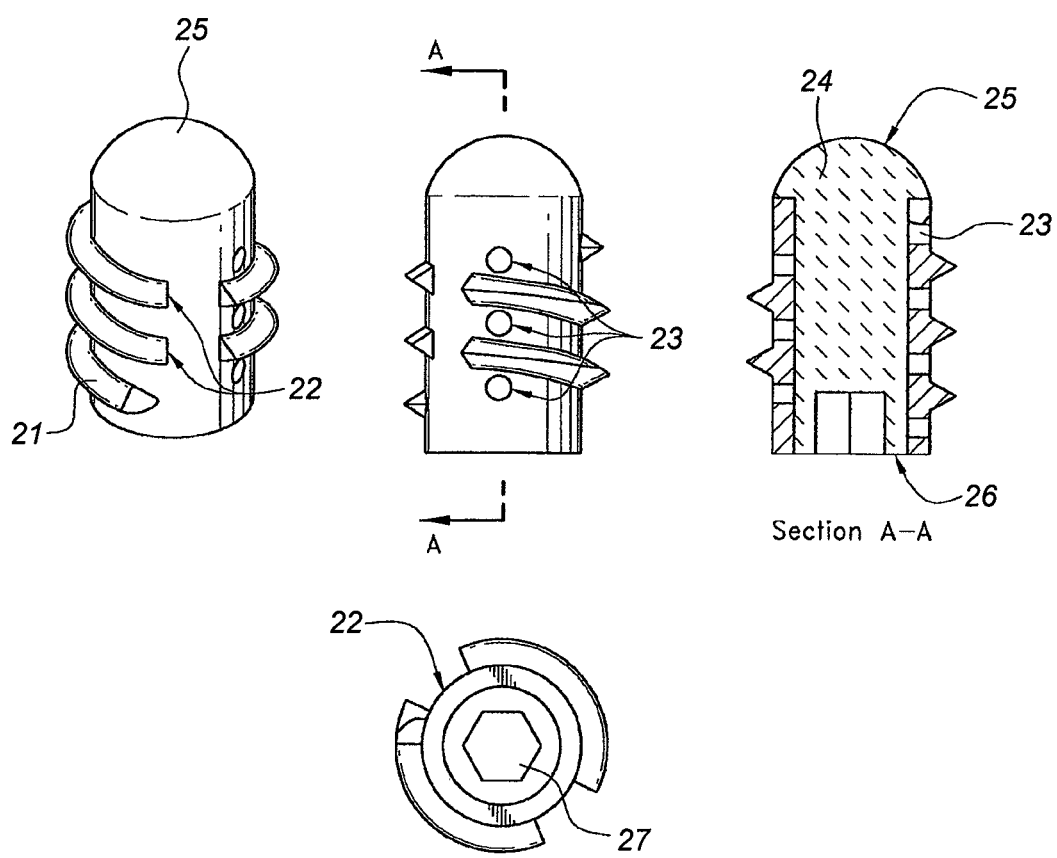
FIG. 2 illustrates, with multiple views, features of the first described device for nutrient transfer.

Referring to FIG. 2, a device is shown that is generally cylindrical in shape having a coarse threaded exterior 21, with periodic interruptions in the thread 22 which allow for stabilization of the device as post placement bony ingrowth occurs. The device will have a core 24 composed of some material such as porous sintered stainless steel, which facilitates the transfer of nutrients from its proximal end 26 to its distal end 25. Additionally, a multiplicity of transverse passages 23 from the exterior surface of the device, to its inner porous core are present to facilitate nutrient transfer. Furthermore, the proximal end 26 of the device will have a feature 27 which accommodates tools utilized for its placement.

Figure 3:
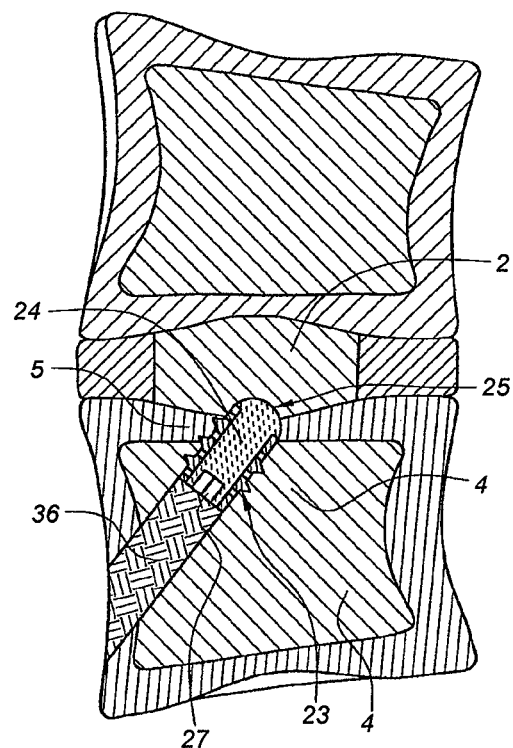
FIG. 3 illustrates, in section view, functional and anatomical aspects of the first described method and device as it relates to the surrounding anatomy after placement.

Referring to FIG. 3, the device is shown post placement such that its distal end 25 is in contact with the nucleus pulposa 2. Cortical and cancellous bone material removed to place the device has been replaced by a substance 36 which will prevent the device from undesired movement after placement. Nutrient transfer will occur from the cancellous bone 4 via the back fill material 36 through the core of the device 24 to the nucleus pulposa 2. Additionally, nutrient transfer will occur from the cancellous bone 4 through passageways 23 along the sides of the device, via the core of the device 24 to the nucleus pulposa 2.

Figure 4:
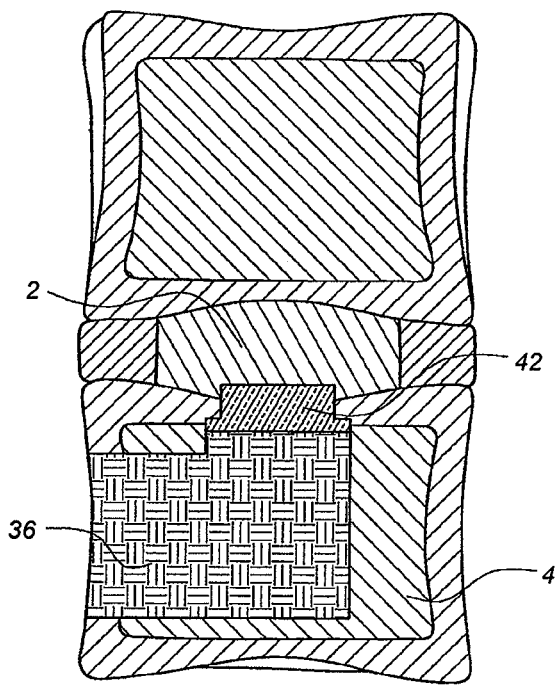
FIG. 4 illustrates, in section view, functional and anatomical aspects of the second described method and device as it relates to the surrounding anatomy after placement.

Referring to FIG. 4, a second device 42 is shown which replaces much of the vertebral body endplate that contacts the nucleus pulposa 2. The cancellous 4 and cortical bone removed to facilitate placement of the device will be replaced with a substance 36, which will serve to both stabilize the device after its placement, and facilitate transport of nutrients to the device from the surrounding cancellous bone 4. The device will allow flow of nutrient material into the nucleus pulposa 2.

Figure 5:
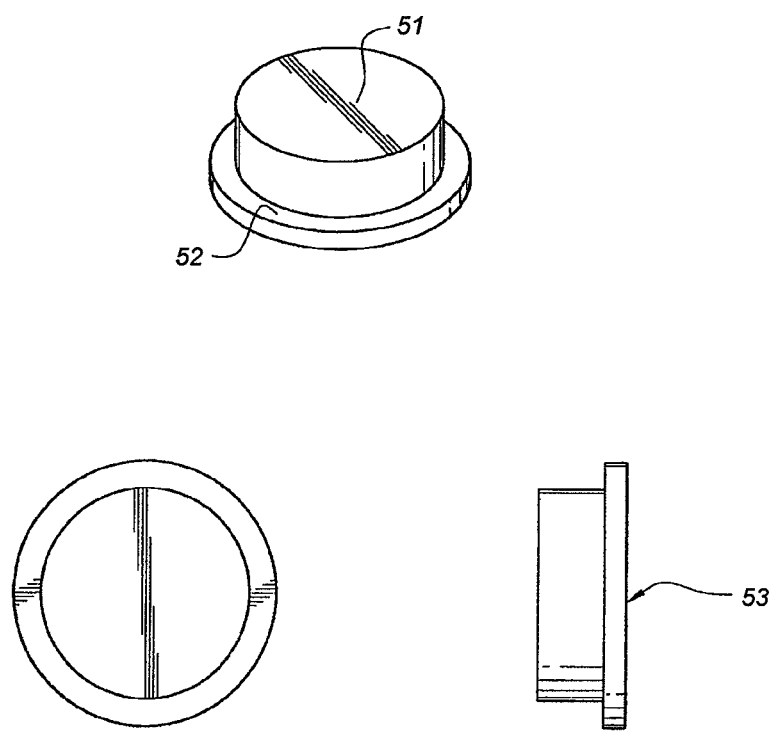
FIG. 5 illustrates, with multiple views, the features of the device disclosed in the second described method.

Referring to FIG. 5, several views are presented of the device shown implanted in FIG. 4. The device has a face 51 that is intended to directly contact the nucleus pulposa, a feature 52 that facilitates appropriate placement in the area where the end plate was removed from the vertebral body, and a second face 53 that will contact back-fill material used to replace the cancellous bone removed from the vertebral body during the placement procedure.

Figure 6:
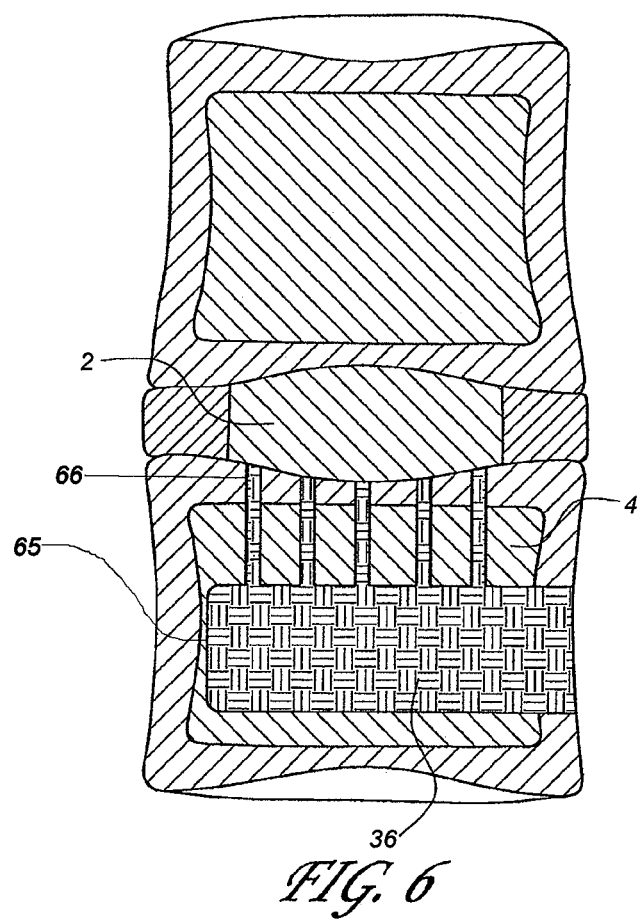
FIG. 6 illustrates, in section view, functional and anatomical aspects of the third described method and device as it relates to the surrounding anatomy after placement.

Referring to FIG. 6, a third method is illustrated for restoration of nutrient flow to the nucleus pulposa 2. A cavity 65 is created to allow a multiplicity of access ports 66 to be drilled to the nucleus pulposa 2. The cavity 65 and the access ports 66 are then filled with a material 36 that facilitates nutrient transfer from the cancellous bone 4 and the tissues surrounding the vertebral body.

Figure 7:
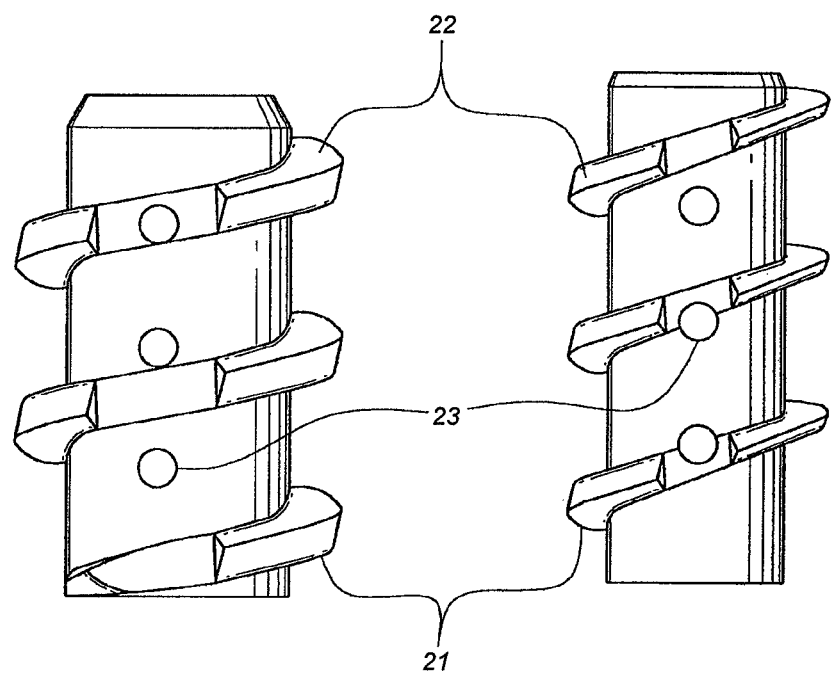
FIG. 7 is an image of the lateral aspect of two different prototype implant devices.

Referring to FIG. 7, two devices are shown that are generally cylindrical in shape having a coarse threaded exterior 21, with periodic interruptions in the thread 22 which allow for stabilization of the device as post placement bony ingrowth occurs. Additionally, a multiplicity of transverse passages 23 from the exterior surface of the device, to its inner porous core are present to facilitate nutrient transfer.

Figure 8:
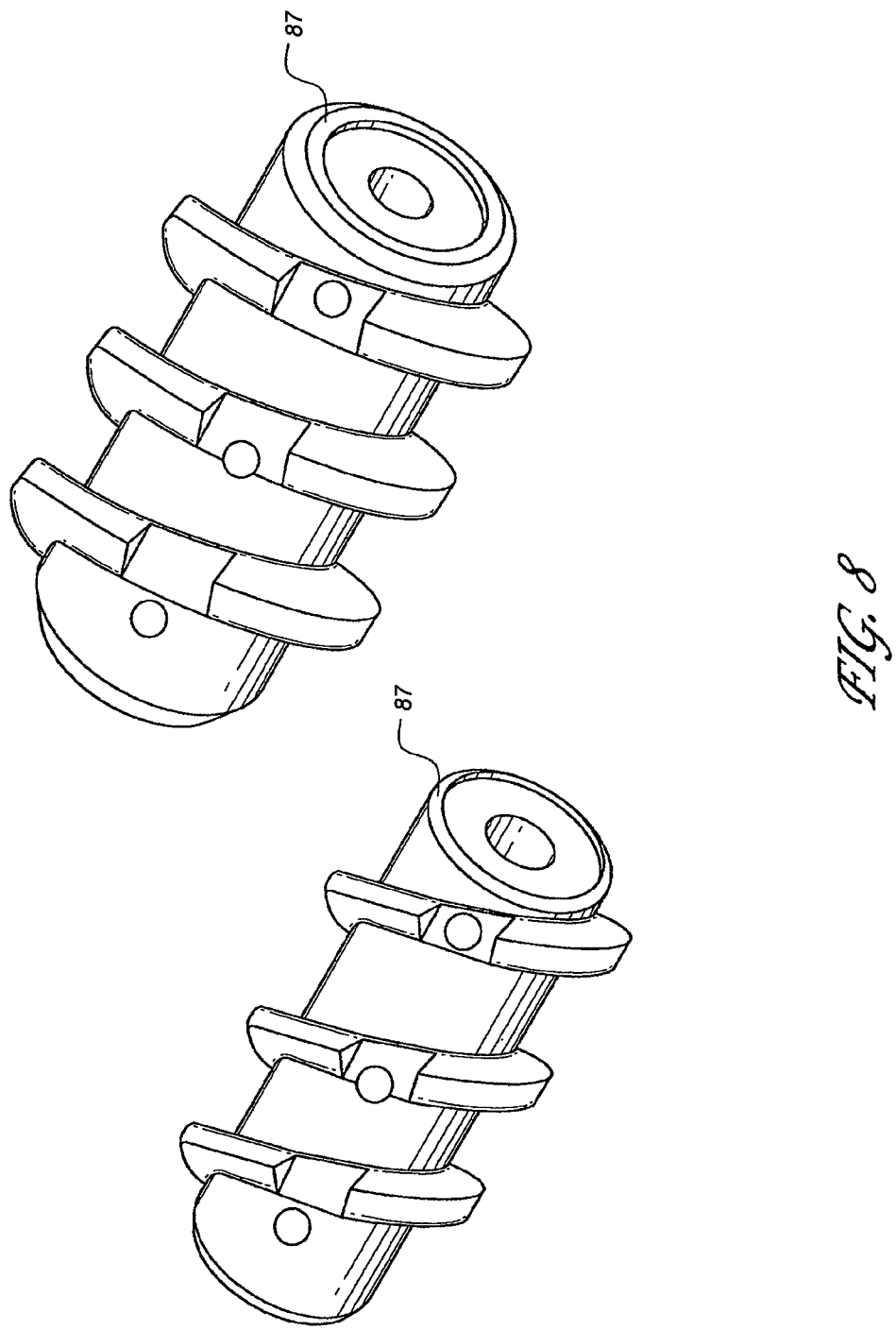
FIG. 8 is an image showing the hexagonal sockets which allow the implants to be screwed into the vertebral body.

Referring to FIG. 8, two devices are shown which have a feature 87 which accommodates tools utilized for its placement.

Figure 9:
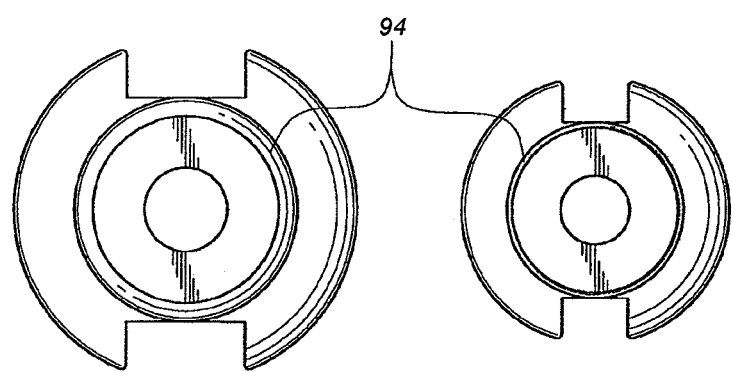
FIG. 9 is an image showing the cavity inside the implants which will be filled with a material that promotes nutrient transfer to the nucleus pulposa.

Referring to FIG. 9, two devices are shown which have a cavity 94, which will be filled with a material such as sintered stainless steel, that promotes the transfer of nutrients to the nucleus pulposa.

In summary, three separate methods and devices are disclosed to restore nutrient flow to the nucleus pulposa. Each of the three described techniques offers the potential to restore normal physiology to the intervertebral disc. Restoration of normal function would eliminate the need for more traumatic surgical techniques such as total disc replacement or spinal fusion. Additionally, these devices and techniques could be used to restore nutrient flow to other avascular tissues such as joint cartilage.

What is claimed is:

1. A method for restoring or establishing nutrient flow to the nucleus pulposa in a spine, comprising the steps of:
    identifying a nucleus pulposa in a patient, the nucleus pulposa surrounded by an upper end plate, a lower end plate and an annulus;
    providing a fluid flow path by accessing the nucleus pulposa via an approach that does not disrupt the annulus, through at least one of the upper end plate and lower end plate to place the nucleus pulposa in flow communication with adjacent tissue;
    implanting a device in an opening in the spine, the device having a first end, a second end, and a fluid flow enabling structure to maintain the fluid flow path through the at least one of the upper end plate and lower end plate to enable nutrient flow to the nucleus pulposa, wherein implanting the device comprises positioning the device such that the first end of the device is in the nucleus pulposa on a first side of the at least one of the upper end plate and lower end plate; and the second end of the device is in fluid communication with tissue on a second side of the at least one of the upper end plate and lower end plate, and
    filling the opening of the spine with backfill material, such that after filling the backfill material facilitates transport of nutrients to the device from surrounding cancellous bone.

2. The method of claim 1, wherein the fluid flow enabling structure comprises a tubular body having the fluid flow path extending therethrough, wherein the tubular body comprises an exterior surface comprising a thread having interruptions, the interruptions intersecting longitudinal axes of the threads.

3. The method of claim 1, wherein providing a fluid flow path comprises providing a fluid flow path through the upper end plate.

4. The method of claim 1, wherein providing a fluid flow path comprises providing a fluid flow path through the lower end plate.

5. The method of claim 2, wherein the interruptions form a first axis that is generally parallel to a second axis, wherein the second axis is the longitudinal axis of the tubular body.

6. The method of claim 2, wherein the interruptions intersect longitudinal axes of the thread and extending generally along the entire axial length of the thread.

7. The method of claim 2, further comprising a plurality of apertures through a side wall of the tubular body.

8. The method of claim 2, wherein the device comprises porous sintered stainless steel.

9. The method of claim 2, wherein the device comprises a feature to accommodate a tool utilized for the placement of the device.

10. The method of claim 9, wherein the feature is on the second end of the device.

11. The method of claim 9, wherein implanting the device comprises connecting the tool to the feature on the device.

12. A method for restoring or establishing nutrient flow to the nucleus pulposa in a spine, comprising the steps of:
    identifying a nucleus pulposa in a patient, the nucleus pulposa surrounded by an upper end plate, a lower end plate and an annulus;
    providing a fluid flow path by accessing the nucleus pulposa via an approach that does not disrupt the annulus, through at least one of the upper end plate and lower end plate to place the nucleus pulposa in flow communication with adjacent tissue;
    implanting a device in an opening in the spine, the device having a first end, a second end, and a fluid flow enabling structure to maintain the fluid flow path through the at least one of the upper end plate and lower end plate to enable nutrient flow to the nucleus pulposa, wherein implanting the device comprises positioning the device such that the first end of the device is in the nucleus pulposa on a first side of the at least one of the upper end plate and lower end plate; and the second end of the device is in operative communication with tissue on a second side of the at least one of the upper end plate and lower end plate, and filling the opening of the spine with backfill material, such that after filling the backfill material facilitates transport of nutrients to the second side of the device from surrounding cancellous bone.

* * * * *